(12) United States Patent
Oh et al.

(10) Patent No.: US 11,272,892 B2
(45) Date of Patent: Mar. 15, 2022

(54) CURVED INTRAORAL SENSOR

(71) Applicant: PICOPACK CO., LTD., Daejeon-si (KR)

(72) Inventors: Guen-young Oh, Daejeon (KR); Dong-Il Kim, Daejeon (KR); Jin-gyu Yang, Daejeon (KR); Gyeong-ho Bae, Daejeon (KR)

(73) Assignee: PICOPACK CO., LTD., Daejeon-si (KR)

( * ) Notice: Subject to any disclaimer, the term of this patent is extended or adjusted under 35 U.S.C. 154(b) by 10 days.

(21) Appl. No.: 16/696,443

(22) Filed: Nov. 26, 2019

(65) Prior Publication Data

US 2021/0145377 A1    May 20, 2021

(30) Foreign Application Priority Data

Nov. 18, 2019  (KR) .................. 10-2019-0147364

(51) Int. Cl.
| | |
|---|---|
| *A61B 6/00* | (2006.01) |
| *A61B 6/12* | (2006.01) |
| *G01T 1/20* | (2006.01) |
| *A61B 6/10* | (2006.01) |

(52) U.S. Cl.
CPC ............. *A61B 6/12* (2013.01); *A61B 6/107* (2013.01); *A61B 6/461* (2013.01); *A61B 6/485* (2013.01); *A61B 6/56* (2013.01); *G01T 1/2006* (2013.01)

(58) Field of Classification Search
None
See application file for complete search history.

(56) References Cited

U.S. PATENT DOCUMENTS

| | | | |
|---|---|---|---|
| 10,825,855 B2* | 11/2020 | Bert | H01L 27/14663 |
| 2002/0106057 A1* | 8/2002 | Halpert | A61B 6/14 378/169 |
| 2006/0262461 A1* | 11/2006 | Wood | H01L 27/14634 361/1 |
| 2016/0113483 A1* | 4/2016 | Uzbelger Feldman | G01T 1/2002 433/29 |
| 2016/0135763 A1* | 5/2016 | Zeller | A61B 6/56 433/29 |
| 2017/0224294 A1* | 8/2017 | Heo | A61B 6/145 |

* cited by examiner

*Primary Examiner* — Hoon K Song
(74) *Attorney, Agent, or Firm* — Novick, Kim & Lee, PLLC; Sang Ho Lee; Hyun Woo Shin

(57) ABSTRACT

Provided is a curved intraoral sensor including a scintillator configured to convert, to an optical signal, an X-ray received by penetrating a subject and to output the optical signal; an image sensor configured to convert the optical signal output from the scintillator to an electrical signal; and a controller configured to receive the electrical signal output from the image sensor, to convert the electrical signal to digital data, and to display an X-ray image of the subject on a screen using the converted digital data. The image sensor includes a first base having a curved surface formed on one surface and a complementary metal-oxide semiconductor (CMOS) formed to correspond to the curved surface on one surface of the first base.

8 Claims, 3 Drawing Sheets

CURVED INTRAORAL SENSOR

CROSS-REFERENCE TO RELATED APPLICATION

This application claims priority to Korea Patent Application No. 10-2019-0147364, filed Nov. 18, 2019, the content of which is incorporated by reference in its entirety.

FIELD OF THE INVENTION

Example embodiments relate to a curved intraoral sensor.

DESCRIPTION OF THE RELATED ART

In dental clinics, medical professionals such as dentists use an X-ray imaging apparatus to determine a dental condition in the oral cavity. This may help to verify detailed dental conditions, for example, small caries, a wisdom tooth, and enlarged periodontal ligament spacing.

Currently, a dental oral sensor that inserts into the oral cavity is in a flat type. The dental oral sensor may be easy to hurt the weak gums with an edge and a patient may experience discomfort due to an irritating hard feeling coming from a foreign body. In particular, infants and babies may cause difficulties in treatment and imaging due to such discomfort.

Accordingly, there is a need for a curved intraoral sensor that may reduce a feeling of irritation and discomfort without causing a degradation in performance at a time of insertion into the oral cavity of a patient.

SUMMARY OF THE INVENTION

At least one example embodiment provides a curved intraoral sensor that may reduce a feeling of irritation and discomfort without causing a degradation in performance at a time of insertion into the oral cavity of a patient.

The aforementioned objects and other objects of the present disclosure may be achieved by the following example embodiments.

According to an aspect of at least one example embodiment, there is provided a curved intraoral sensor including a scintillator configured to convert, to an optical signal, an X-ray received by penetrating a subject and to output the optical signal; an image sensor configured to convert the optical signal output from the scintillator to an electrical signal; and a controller configured to receive the electrical signal output from the image sensor, to convert the electrical signal to digital data, and to display an X-ray image of the subject on a screen using the converted digital data. The image sensor includes a first base having a curved surface formed on one surface and a complementary metal-oxide semiconductor (CMOS) formed to correspond to the curved surface on one surface of the first base.

A curvature of the curved surface may have a change of 8° to 12° (an angle a) relative to a length (L) of 35 mm to 45 mm.

A thickness of the CMOS may be 0.2 mm to 0.3 mm.

The CMOS may be configured to go through a backgrinding process.

The scintillator may have a thickness of 0.2 mm to 0.4 mm, and may include gadolinium oxysulfide (GOS).

The curved intraoral sensor may further include a second base formed on a surface of the controller that faces the image sensor. The second base may include stainless steel (SUS).

The curved intraoral sensor may further include a cover configured to cover a region corresponding to a side of the curved intraoral sensor and the scintillator, excluding a region corresponding to the second base. The cover may include at least one of carbon fiber reinforced plastics (CFRP), long fiber reinforced thermoplastics (LFT), and continuous fiber reinforced thermoplastics (CFRTPC).

The curved intraoral sensor may be protected with a case configured to surround an outermost surface of the curved intraoral sensor, and the case may include hard silicon.

The curved intraoral sensor may further include a collimator provided between the scintillator and the image sensor. The collimator may include a first film layer; and a blind layer including penetration layers each printed in transparent ink and configured to transmit an image in a region excluding shielding partition formation spaces iteratively provided at desired intervals to be in parallel or in a grid shape on the first film layer and shielding partitions formed by filling light absorbing colored ink in the shielding partition formation spaces.

The shielding partition may have a width of 5 μm to 50 μm and have a height of 10 μm to 150 μm, and an interval between the shielding partitions may be 20 μm to 130 μm.

According to some example embodiments, there may be provided a curved intraoral sensor that may reduce a feeling of irritation and discomfort without causing a degradation in performance at a time of insertion into the oral cavity of a patient.

Further areas of applicability will become apparent from the description provided herein. The description and specific examples in this summary are intended for purposes of illustration only and are not intended to limit the scope of the present disclosure.

BRIEF DESCRIPTION OF DRAWINGS

These and/or other aspects, features, and advantages of the invention will become apparent and more readily appreciated from the following description of embodiments, taken in conjunction with the accompanying drawings of which.

DETAILED DESCRIPTION OF THE INVENTION

Figure 1:
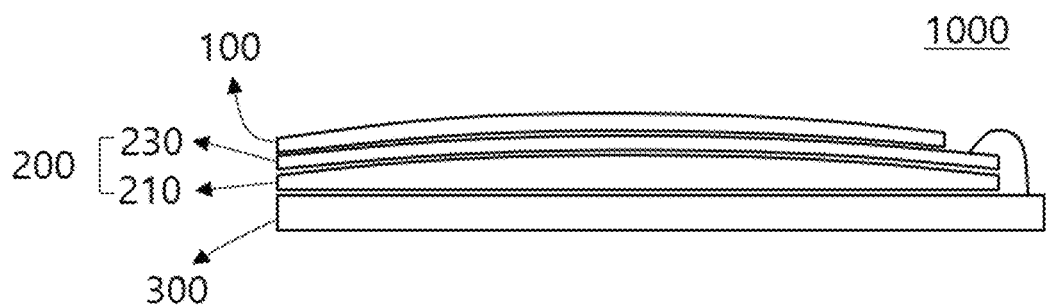
FIG. 1 is a cross-sectional view of a curved intraoral sensor according to an example embodiment.

One or more example embodiments will be described with reference to the accompanying drawings. Advantages and features of the example embodiments, and methods for achieving the same may become explicit by referring to the accompanying drawings and the following example embodiments. Example embodiments, however, may be embodied in various different forms, and should not be construed as being limited to only the illustrated embodiments.

Rather, the illustrated embodiments are provided as examples so that this disclosure will be thorough and complete, and will fully convey the concepts of this disclosure to those skilled in the art. Sizes of components, such as widths, thicknesses, etc., may be exaggerated to clearly represent the components of each apparatus in the drawings. Also, although only a portion of the components are illustrated for clarity of description, one of ordinary skill in the art may easily verify the remaining components.

When an element is referred to as being on or below another element, the element may be directly on or below the other element or an intervening element may be present between the elements. Also, one of ordinary skill in the art may embody the spirit of the present application in various forms without departing from the scope of technical spirit. Unless otherwise noted, like reference characters denote like elements throughout the attached drawings and written description, and thus descriptions will not be repeated.

As used herein, the singular forms "a," "an," and "the," are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups, thereof.

Although the terms "first," "second," "third," etc., may be used herein to describe various elements, components, regions, layers, and/or sections, these elements, components, regions, layers, and/or sections, should not be limited by these terms. These terms are only used to distinguish one element, component, region, layer, or section, from another region, layer, or section. Thus, a first element, component, region, layer, or section, discussed below may be termed a second element, component, region, layer, or section, without departing from the scope of this disclosure.

Also, "X to Y" representing the range indicates "greater than or equal X and less than or equal to Y".

When an element is referred to as being "connected to" another element, the element may be directly connected to the other element, and may be "electrically connected to" the other element using an intervening element present therebetween.

Also, although the respective stacked structures are slightly separate to clearly represent the respective stacked structures in the drawings, they may be in contact with each other and may be stacked by using an adhesive layer, for example, an epoxy adhesive layer, provided between the layered structures as a medium.

Curved Intraoral Sensor

Hereinafter, a curved intraoral sensor according to an example embodiment is described.

FIG. 1 is a cross-sectional view of a curved intraoral sensor according to an example embodiment.

Referring to FIG. 1, a curved intraoral sensor 1000 according to an example embodiment may include a scintillator 100 configured to covert, to an optical signal, an X-ray received by penetrating a subject and to output the optical signal; an image sensor 200 configured to convert the optical signal output from the scintillator 100 to an electrical signal; and a controller 300 configured to receive the electrical signal output from the image sensor 200, to convert the electrical signal to digital data, and to display an X-ray image of the subject on a screen using the converted digital data. The image sensor 200 may include a first base 210 having a curved surface formed on one surface and a complementary metal-oxide semiconductor (CMOS) 230 formed to correspond to the curved surface on one surface of the first base 210.

The scintillator 100 serves to receive the X-ray that penetrates the subject, to convert the received X-ray to the optical signal, and to output the converted optical signal. Here, the X-ray may be received from above in FIG. 1. A phosphor scintillator material used to form the scintillator 100 may be a material used to intensify a screen image, and may be, for example, at least one of gadolinium oxysulfide doped with at least one of terbium and europium; barium fluorochloride doped with at least one of yttrium oxide, calcium tungsten, and europium; barium sulfate doped with at least one of terbium, thulium, and dysprosium; strontium sulfate; and zinc sulfide.

The scintillator 100 may be manufactured in a screen form and may transfer the converted optical signal to the image sensor 200. Here, the material, scintillator, refers to ionized particles or a material that emits light after a shock of gamma-quanta. Further description related thereto is omitted.

For example, the scintillator 100 may have a thickness of 0.2 mm to 0.4 mm and may include gadolinium oxysulfide (GOS). Here, it is possible to enhance an optical signal conversion efficiency and to achieve a miniaturization of the curved intraoral sensor 1000.

The image sensor 200 serves to convert the optical signal output from the scintillator 100 to the electrical signal. Herein, the image sensor 200 may include the first base 210 having a curved surface on one surface, for example, in a direction in which the X-ray is received, and the CMOS 230 formed to correspond to the curved surface on one surface of the first base 210. Accordingly, in the curved intraoral sensor 1000, a portion contacting with the gums or teeth is curved and thus, it is possible to prevent the gums from being hurt by an edge and to reduce a feeling of irritation and discomfort at a time of insertion into the oral cavity of a patient.

Figure 2:
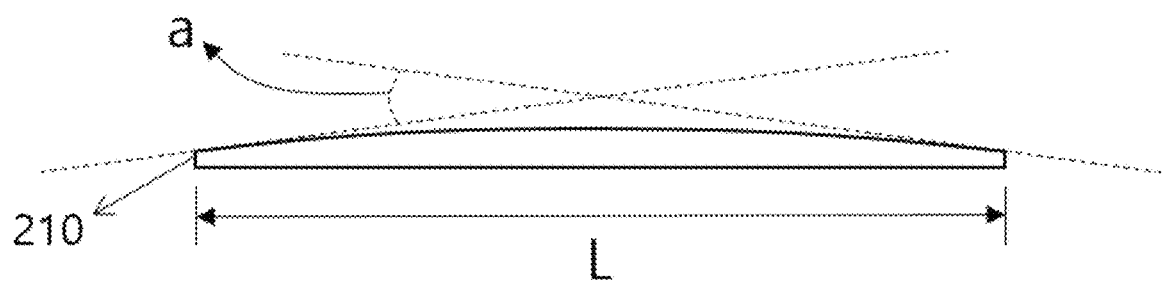
FIG. 2 is a cross-sectional view of an image sensor of a curved intraoral sensor according to an example embodiment.

FIG. 2 is a cross-sectional view of an image sensor of a curved intraoral sensor according to an example embodiment.

Referring to FIG. 2, a curvature of the curved surface of the first base 210 may have a change of 8° to 12° (angle a) relative to a length L of 35 mm to 45 mm. In this range, the curved intraoral sensor 1000 may minimize a stimulus to the gums and teeth and to reduce a feeling of irritation of a patient.

Due to the curvature of the first base 210, the CMOS 230 and the scintillator 100 may be formed at the substantially identical curvature.

The first base 210 may be configured as stainless steel (SUS), which may lead to stably fastening a structure of the CMOS 230 having a curved surface and minimizing deformation. Also, it is possible to radiate heat generated in response to an operation of the curved intraoral sensor 1000.

A central portion of the first base 210 may have a thickness of 1.5 mm to 3.5 mm, in detail, for example, a thickness of 2 mm to 3 mm. In this range, it is possible to achieve relatively excellent balancing in terms of CMOS fastening, deformation prevention, and heat radiation effect.

The CMOS 230 serves to convert the optical signal transferred from the scintillator 100 to the electrical signal and to output the electrical signal. That is, the CMOS 230 may convert an X-ray image of the subject to be photographed to digital data. Here, the CMOS 230 may electrically connect to the controller 300 and may transfer a digital data signal to the controller 300.

The CMOS 230 may have a thickness of 0.2 mm to 0.3 mm, and may have gone through a backgrinding process.

Herein, by applying the CMOS 230 as a configuration of the image sensor 200, fast signal processing may be achieved and the curved surface may be formed with a reduced thickness by backgrinding.

The CMOS 230 may be stacked on the first base 210 by using a hard epoxy adhesive layer as a medium. After curing, the hard epoxy adhesive layer may have a die shear value of 2 kg (711 psi) or more at 23° C. In this range, the CMOS 230 may be stably fastened to the first base 210 and may minimize a delamination.

The image sensor 200 and the scintillator 100 may be stacked by using a soft epoxy adhesive layer as a medium. In this case, a work process may be easy.

The controller 300 serves to receive the electrical signal output from the CMOS 230 of the image sensor 200, to convert the X-ray image of the subject to digital data, to store the X-ray image of the subject in a storage device provided in an apparatus or a separate storage device based on the converted digital data, and to display the stored digital data on a screen through an image processing process.

In detail, for example, in response to a user selection, the controller 300 may output the X-ray image of the subject converted to the digital data using an output device, for example, a printer. For miniaturization of the curved intraoral sensor 1000, only a minimum configuration for control may be provided to the controller 300 of FIG. 1 and the controller 300 may perform a necessary processing process through a cable connection with an outside. That is, the controller 300 may include a configuration stacked in the curved intraoral sensor 1000 and a configuration connected through a separate cable.

It is evident to those skilled in the art that the controller 300 may include any technology capable of converting an analog signal to a digital signal and processing an image using converted digital data.

Figure 3:
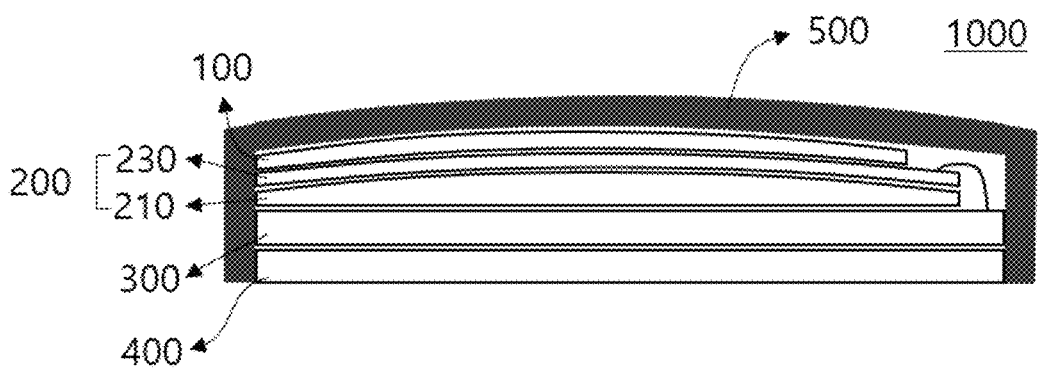
FIG. 3 is a cross-sectional view of a curved intraoral sensor according to an example embodiment.

FIG. 3 is a cross-sectional view of a curved intraoral sensor according to an example embodiment.

Referring to FIG. 3, the curved intraoral sensor 1000 may further include a second base 400 formed on (below) a surface of the controller 300 to face the image sensor 200, and the second base 400 may include stainless steel (SUS).

The second base 400 may have a thickness of 0.8 mm to 1.2 mm and may include stainless steel (SUS). Here, the second base 400 may protect the curved intraoral sensor 1000 and thereby enhance a durability. Also, it is possible to prevent a bending phenomenon even against heat radiation by the curved intraoral sensor 1000 and to achieve a relatively excellent heat radiation effect.

Also, the second base 400 may be stacked by providing an adhesive layer between the controller 300 and the second base 400 as a medium.

The curved intraoral sensor 1000 may further include a cover 500 configured to cover a region corresponding to a side of the curved intraoral sensor 1000 and the scintillator 100, excluding a region corresponding to the second base 400.

The cover 500 serves to provide a space in which each configuration may be easily stacked during a curved intraoral sensor manufacturing process. Also, the cover 500 may be formed at the substantially same curvature as that of the curved surface of the first base 210. In this case, it is possible to prevent delamination of the CMOS 230 from the first base 210 due to stacking and to prevent even an external impact.

The cover 500 may be formed with a thickness of 0.3 mm to 0.7 mm, and the cover 500 may be stacked by providing a soft epoxy adhesive layer between the scintillator 100 and the cover 500 as a medium.

The cover 500 may include at least one of carbon fiber reinforced plastic (CFRP), long fiber reinforced thermoplastic (LFT), and continuous fiber reinforced thermoplastic (CFRTPC).

Figure 4:
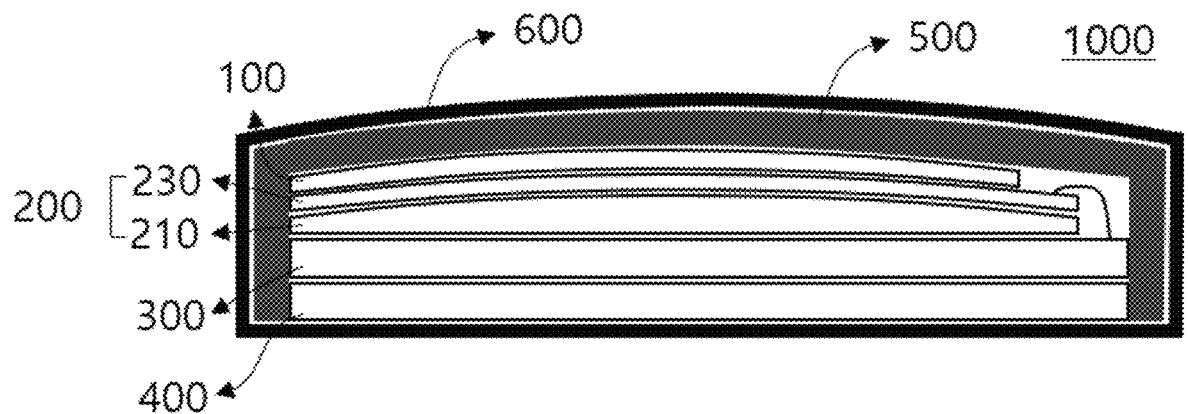
FIG. 4 is a cross-sectional view of a curved intraoral sensor according to an example embodiment.

FIG. 4 is a cross-sectional view of a curved intraoral sensor according to an example embodiment.

Referring to FIG. 4, the curved intraoral sensor 1000 may be protected with a case 600 configured to surround an outermost surface of the curved intraoral sensor 1000, and the case 600 may include hard silicon.

Since the case 600 includes hard silicon, it is possible to primarily prevent an external impact and to minimize a feeling of irritation of a patient.

A hardness (shore A) of hard silicon may be 45 to 80. In this range, it is possible to achieve a relatively excellent balancing in terms of external impact prevention and irritating feeling minimization effect.

Figure 5:
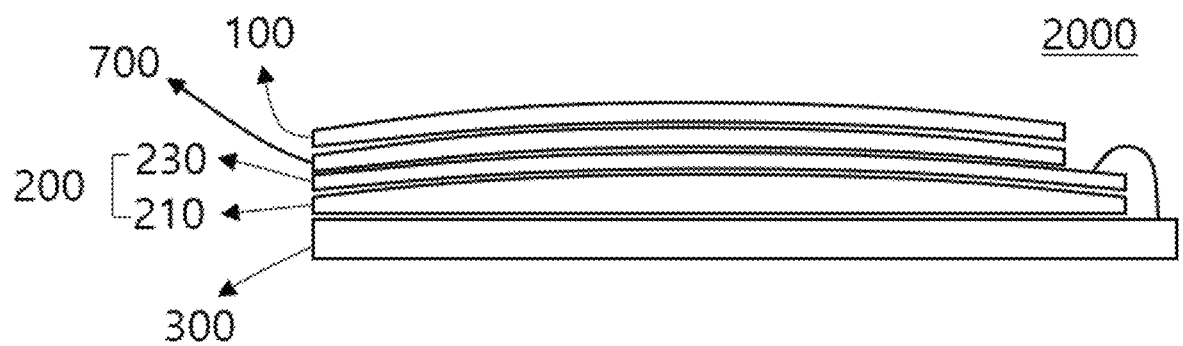
FIG. 5 is a cross-sectional view of a curved intraoral sensor according to another example embodiment.

Hereinafter, a curved intraoral sensor according to another example embodiment is described with reference to FIGS. 5 and 6. FIG. 5 is a cross-sectional view of a curved intraoral sensor according to another example embodiment, and FIG. 6 is a cross-sectional view of a collimator of a curved intraoral sensor according to another example embodiment.

Figure 6:
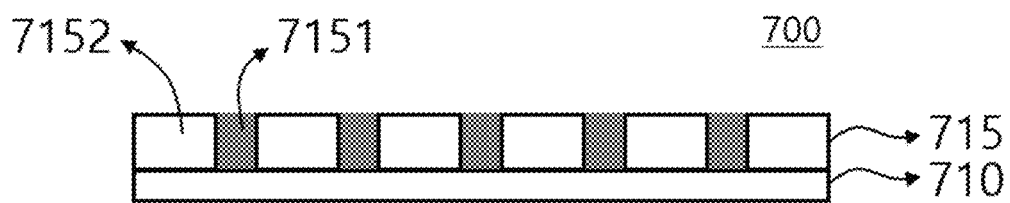
FIG. 6 is a cross-sectional view of a collimator of a curved intraoral sensor according to another example embodiment.

Referring to FIGS. 5 and 6, a curved intraoral sensor 2000 may further include a collimator 700 provided between a scintillator 100 and an image sensor 200. The collimator 700 may include a first film layer 710; and a blind layer 715 including penetration layers 7152 each printed in transparent ink and configured to transmit an image in a region excluding shielding partition formation spaces 7151 iteratively provided at desired intervals to be in parallel or in a grid shape on the first film layer 710 and shielding partitions 7151 formed by filling light absorbing colored ink in the shielding partition formation spaces 7151.

In general, an X-ray sensor may include a light transmitter, for example, a fiber of plate (FOP) formed of an optical fiber between a scintillator and an image sensor. However, this configuration may not apply when the image sensor 200 and the scintillator 100 of the present disclosure are curved as herein.

Accordingly, the collimator 700 suitable for the curved intraoral sensor 2000 may be applied herein. The collimator 700 may prevent interference between optical signals output from the scintillator 100, thereby acquiring a further clear and high resolution image.

The first film layer 710 may prepare a formation space of the blind layer 715 and may be bendable to correspond to a curvature of the first base 210.

The first film layer 710 may include at least one of polypropylene oxide, polyisocyanate, hydroxyethyl, monoacrylate, polyacrylate, polymethylmethacrylate, polyurethane, methacrylate, polypropylene, cellulose acetate butylate (CAB), ethylene-vinyl acetate (EVA), polyvinyl alcohol (PVA), acrylate, hydroxyethyl, and propylene oxide.

For example, the first film layer 710 may include polypropylene oxide, and may be formed with a thickness of 10 μm to 500 μm, in detail, for example, a thickness of 50 μm to 300 μm, in more detail, a thickness of 150 μm to 250 μm. In this range, the curved surface may be readily formed and a relatively excellent collimation effect may be achieved.

The penetration layer 7152 may include a process of printing transparent ink in the first film layer 710. In detail, a single process may be selected from among a fine precision printing process, a ultraviolet (UV) printing process, a roll-to-roll printing process, a printing electronic process, a flat screen process, a roll screen process, a printed circuit board (PCB) screen process, an offset process, and a gravure process. For example, in response to a selection on a flat screen printing process, a penetration layer pattern may be formed in a region excluding a region in which a shielding partition is to be formed by applying a fine printing process and by printing transparent ink using squeeze or blade.

The penetration layer 7152 may be formed using transparent ink capable of transmitting a picture image and may be formed using UV ink or solvent ink. Also, UV ink may be used for fast curing.

The transparent ink used to form the penetration layer 7152 may include resin and may selectively include a solvent, a polymerization initiator, a viscosity improver, an antioxidant, a wetting aid, a dispersant, a polymerization inhibitor, a sensitizer, and the like. A pigment that is a colorant generally included in the ink is not included to ensure transparency, but may be included to some extent depending on the intended use.

The resin may include polypropylene oxide, polyethylene, polypropylene, ethylene-vinyl acetate (EVA), polyvinyl alcohol (PVA), polyvinyl chloride (PVC), polyethylene terephthalate (PET), cellulose acetate butyrate (CAB), monoacrylate polyacrylate, polymethyl methacrylate, polyurethane, polycarbonate, propylene oxide, polyisocyanate, hydroxyethyl acrylate, hydroxyethyl methacrylate, or copolymers thereof.

The penetration layers 7152 may be formed in a region excluding pattern shapes in which the shielding partitions 7151 are to be formed, and may be formed by iteratively providing the shielding partitions 7151 at desired intervals or to be in parallel or in a grid shape.

The shielding partition 7151 may have a width of 5 μm to 50 μm and a height of 10 μm to 150 μm, and an interval between the shielding partitions 7151 may be 20 μm to 130 μm. In the shielding partition range and the first film layer thickness range, a relatively excellent collimation effect may be achieved.

The shielding partitions 7151 may be provided in parallel or in a grid shape at desired intervals and at a desired angle and may be formed using light absorbing colored ink. The width, the height, and the interval of the shielding partition 7151 may be determined based on a mutual optical interaction.

According to an example embodiment, the shielding partition 7151 may have a relatively high absorbance to ensure a sufficient blocking property. The shielding partition 7151 may be formed using colored ink capable of blocking an image and may be formed using UV ink or solvent ink. Also, UV ink may be for fast curing. In the case of using UV ink, instantaneous curing is performed by filling transparent and colored UV ink and, at the same time, irradiating a UV lamp.

Also, colored ink used to form the shielding partition 7151 may include a pigment and resin and may selectively include a solvent, a polymerization initiator, a viscosity improver, an antioxidant, a wetting aid, a dispersant, a polymerization inhibitor, a sensitizer, and the like.

Here, the pigment may use an organic or inorganic pigment or dye. The organic pigment may be used to form a high concentration shieling and the inorganic pigment may be used to form a low concentration shielding. In particular, in the case of mixing a pigment having a high concentration and a high absorbance with a pigment having a low concentration and a low absorbance capable of preventing a diffused reflection, it is possible to provide a clear image by blocking a distorted image output of a security film. Here, colored ink may have a particle size of about 2 nm to 18 μm.

The resin may include polypropylene oxide, polyethylene, polypropylene, ethylene-vinyl acetate (EVA), polyvinyl alcohol (PVA), polyvinyl chloride (PVC), polyethylene terephthalate (PET), cellulose acetate butyrate (CAB), monoacrylate polyacrylate, polymethyl methacrylate, polyurethane, polycarbonate, propylene oxide, polyisocyanate, hydroxyethyl acrylate, hydroxyethyl methacrylate, or copolymers thereof.

Meanwhile, the shielding partition 7151 may be formed on a surface of the first film layer 710 by filling colored ink in a region on which the penetration layer 7152 is not formed through squeeze or blade.

As another example, the shielding partition 7151 may be formed on one surface or both surfaces of the first film layer 710. Here, when the shielding partition 7151 is formed on each of both surfaces of the first film layer 710, the shielding partitions 7151 may be formed at the same position on both surfaces of the first film layer 710, thereby achieving a thickness extension effect through mutual overlapping.

Figure 7:
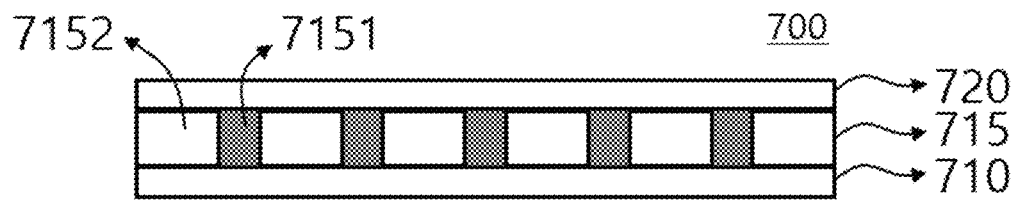
FIG. 7 is a cross-sectional view of a collimator of a curved intraoral sensor according to an example embodiment.

Referring to FIG. 7, as another example, the collimator 700 may reinforce a structure by forming a second film layer 720 on the blind layer 715. The second film layer 720 may use the substantially same material as that of the first film layer 710.

Curved Intraoral Sensor Manufacturing Method

Hereinafter, a method of manufacturing a curved intraoral sensor according to an example embodiment is described. In the following description, the respective components may be substantially identical to the aforementioned components of the curved intraoral sensor.

The method of manufacturing a curved intraoral sensor according to the example embodiment may include forming a curved surface with a curvature having a change of 8° to 12° (angle a) relative to a length (L) of 35 mm to 45 mm on one surface of the first base 210; backgrinding the CMOS 230 at a thickness of 0.2 mm to 0.3 mm; preparing the image sensor 200 by attaching the backgrinding processed CMOS 230 on the first base 210 by providing a hard epoxying adhesive layer therebetween as a medium; stacking the image sensor 200 on the controller 300 by providing a hard epoxy adhesive layer therebetween as a medium and then connecting a signal using a gold wire; stacking the second base 400 on the controller 300; stacking the scintillator 100 on the image sensor 200 by providing a soft epoxy adhesive layer therebetween as a medium; bonding and thereby fastening the assembly within the cover 500; and forming the case 600.

In the backgrinding, the CMOS 230 may go through a backgrinding process to be from a thickness of 0.725 mm to be 0.2 mm to 0.3 mm. In this case, the optical signal conversion efficiency of the CMOS 230 may be maintained, the curved surface may be stably formed and fastened on the first base 210, and a delamination may be excellently prevented.

A zig may be used to stack the first base 210 and the CMOS 230.

As another example, the collimator 700 may be stacked on the image sensor 200 prior to stacking the scintillator 100. The aforementioned description may apply to the collimator 700 here.

Figure 8:
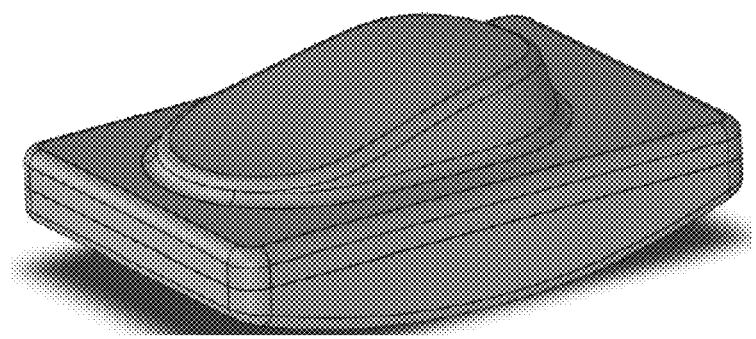
FIG. 8 illustrates an example of manufacturing a curved intraoral sensor according to an example embodiment.
Figure 9:
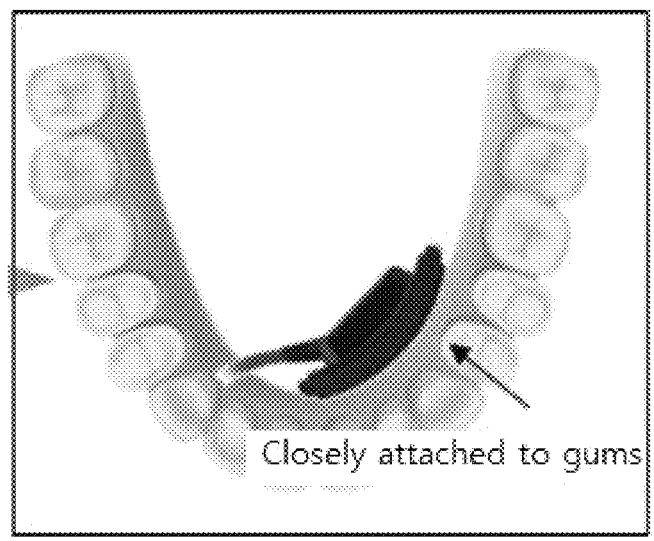
FIG. 9 illustrates an example of using a curved intraoral sensor according to an example embodiment.

Referring to FIGS. 8 and 9, a curved intraoral sensor of the present disclosure manufactured through the aforementioned manufacturing process may be in a shape of FIG. 8, and may prevent the gums from being hurt by an edge within the oral cavity and may reduce a feeling of irritation and discomfort at a time of insertion into the oral cavity of a patient.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A curved intraoral sensor comprising:
   a scintillator configured to convert, to an optical signal, an X-ray received by penetrating a subject and to output the optical signal;
   an image sensor configured to convert the optical signal output from the scintillator to an electrical signal;
   a controller configured to receive the electrical signal output from the image sensor, to convert the electrical signal to digital data, and to display an X-ray image of the subject on a screen using the converted digital data; and
   a collimator provided between the scintillator and the image sensor,
   wherein the image sensor comprises a first base having a curved surface formed on one surface toward the scintillator and a complementary metal-oxide semiconductor (CMOS) formed to correspond to the curved surface on one surface of the first base,
   wherein a curvature of the curved surface has a change of 8° to 12° relative to a length of 35 mm to 45 mm of the first base,
   wherein the first base comprises stainless steel (SUS),
   wherein the collimator comprises:
   a first film layer; and
   a blind layer comprising penetration layers each printed in transparent ink and configured to transmit an image in a region excluding shielding partition formation spaces iteratively provided at desired intervals to be in parallel or in a grid shape on the first film layer and shielding partitions formed by filling light absorbing colored ink in the shielding partition formation spaces,
   wherein the shielding partition has a width of 5 μm to 50 μm and has a height of 10 μm to 150 μm, and an interval between the shielding partitions is 20 μm to 130 μm, and
   wherein a surface of the first base disposed opposite to the curved surface and towards the controller is planar, and a surface of the controller facing the planar surface of the first base is planar.

2. The curved intraoral sensor of claim 1, wherein a thickness of the CMOS is 0.2 mm to 0.3 mm.

3. The curved intraoral sensor of claim 2, wherein the CMOS is configured to go through a backgrinding process.

4. The curved intraoral sensor of claim 1, wherein the scintillator has a thickness of 0.2 mm to 0.4 mm, and comprises gadolinium oxysulfide (GOS).

5. The curved intraoral sensor of claim 1, further comprising:
   a second base formed on a surface of the controller that faces the image sensor,
   wherein the second base comprises stainless steel (SUS).

6. The curved intraoral sensor of claim 5, further comprising:
   a cover configured to cover a region corresponding to a side of the curved intraoral sensor and the scintillator, excluding a region corresponding to the second base,
   wherein the cover comprises at least one of carbon fiber reinforced plastic (CFRP), long fiber reinforced thermoplastic (LFT), and continuous fiber reinforced thermoplastic (CFRTPC).

7. The curved intraoral sensor of claim 1, wherein
   the curved intraoral sensor is protected with a case configured to surround an outermost surface of the curved intraoral sensor, and
   the case comprises hard silicon.

8. The curved intraoral sensor of claim 1, wherein the CMOS and the scintillator each have a curvature substantially identical to the curvature of the curved surface of the first base.

* * * * *